United States Patent
Pan et al.

(10) Patent No.: US 10,073,945 B1
(45) Date of Patent: Sep. 11, 2018

(54) PROCESS FOR EVALUATING SKIN CARE PRODUCT EFFICACY AND SKIN CARE PRODUCT EFFICACY EVALUATION SYSTEM

(71) Applicants: Ning Pan, Davis, CA (US); Hualin Huang, Davis, CA (US)

(72) Inventors: Ning Pan, Davis, CA (US); Hualin Huang, Davis, CA (US)

(*) Notice: Subject to any disclaimer, the term of this patent is extended or adjusted under 35 U.S.C. 154(b) by 147 days.

(21) Appl. No.: 15/149,000

(22) Filed: May 6, 2016

Related U.S. Application Data

(60) Provisional application No. 62/157,739, filed on May 6, 2015.

(51) Int. Cl.
*G01N 37/00* (2006.01)
*G06F 19/12* (2011.01)

(52) U.S. Cl.
CPC .................... *G06F 19/12* (2013.01)

(58) Field of Classification Search
CPC ................. G06F 19/00; G06F 17/60
See application file for complete search history.

(56) References Cited

U.S. PATENT DOCUMENTS

2003/0093297 A1* 5/2003 Schilling ............... G06Q 30/02
  705/2
2010/0249731 A1* 9/2010 Stamatas .............. A61B 5/0059
  604/290

* cited by examiner

*Primary Examiner* — Elias Desta
(74) *Attorney, Agent, or Firm* — Plager Schack LLP; Mark H. Plager

(57) ABSTRACT

An instrumental approach enabling evaluation of efficacy of skin care products is disclosed. Common problems shared by existing methods include first the difficulty whether to test the entire human face, or just focus on the key locations (not determined yet); the difficulty in conducting a repeatable test when human face is hard to fix on and changes between different persons; and how many different skin attributes to test for making a reliable and complete judgment. The instrumental approach of the process tests a sample at once to obtain all the information needed. It shows good repeatability and sensitivity. It yields necessary yet sufficient information in numbers.

10 Claims, 7 Drawing Sheets

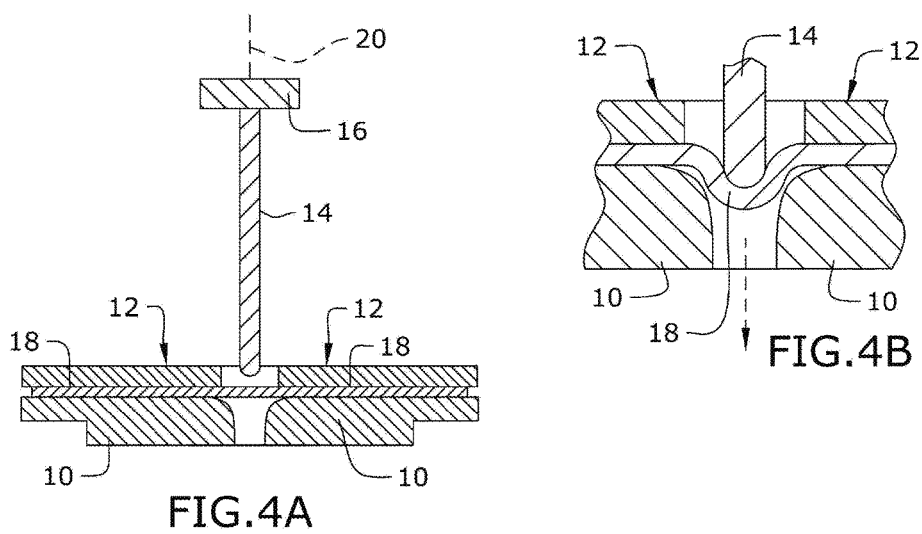
FIG.4A
FIG.4B
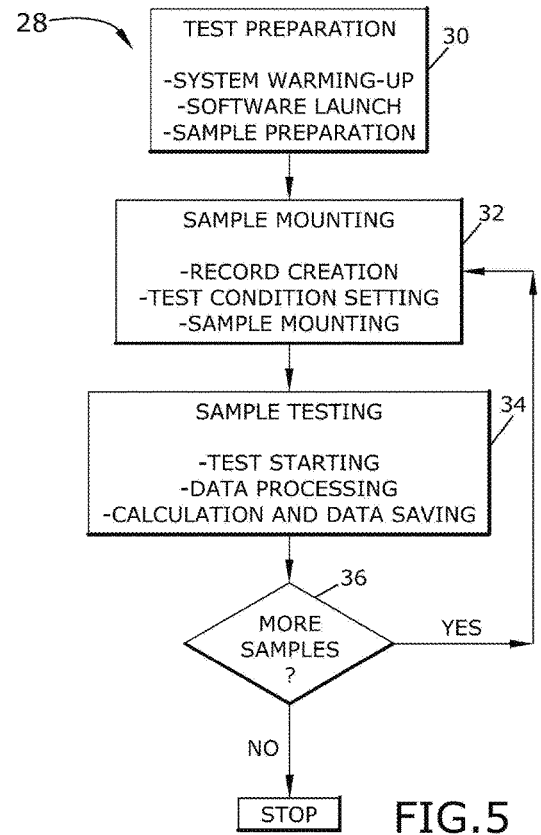
FIG.5

PROCESS FOR EVALUATING SKIN CARE PRODUCT EFFICACY AND SKIN CARE PRODUCT EFFICACY EVALUATION SYSTEM

CLAIM OF BENEFIT TO PRIOR APPLICATION

This application claims benefit to U.S. Provisional Patent Application 62/157,739, entitled "An instrument enabling evaluation of efficacy of skin care products," filed May 6, 2015. The U.S. Provisional Patent Application 62/157,739 is incorporated herein by reference.

BACKGROUND

Embodiments of the invention described in this specification relate generally to methods of testing skin care products, and more particularly, to a skin care product efficacy evaluation system and a process for evaluating skin care product efficacy by an instrumental approach to testing skin care products.

Skin protection and improvement are claims made by manufacturers of all skin care products. However, there are no effective methods to test or validate these claims.

Human detection and discretion for changes in skin attributes are unreliable. Several existing instruments have been tried but, to date, none of the existing instruments are successful at objectively evaluating and detecting improvements in skin protection, skin quality, and other such skin attributes. Furthermore, previous methods have relied on subjective evaluation of skin care products, or have been based on unreliable approaches to instrumentation-based testing.

Therefore, what is needed is an instrumental approach to testing skin care products and evaluating the efficacy of the instrumentally tested skin care products.

BRIEF DESCRIPTION

The disclosed invention includes a skin care product efficacy evaluation system and a process for evaluating skin care product efficacy by an instrumental approach to testing skin care products. The instrumental approach includes using an instrument that measures sensory properties and attributes of skin, synthetic skin, skin specimens, and/or other fibrous specimens.

In some embodiments, the process for evaluating efficacy of skin care products is performed by using a phabrometer to test samples with skin care products applied. In some embodiments, the process for evaluating efficacy of skin care products includes selecting a substrate treated with a skin care product. In some embodiments, the substrate includes a synthetic skin specimen. In some embodiments, after the selected substrate is treated with the skin care product, the process then tests the substrate by using the phabrometer to show skin performance numerically in terms of skin attributes, including skin softness, skin smoothness, skin resilience, and wrinkle resistance. In some embodiments, the phabrometer includes a computerized smart machine that tests a specimen quickly and analyzes the result based on an algorithm, and provides the outputs necessary and sufficient to completely characterize the skin performance.

In some embodiments, the skin care product efficacy evaluation system provides a cloud-network service for evaluating efficacy of skin care products based on numerical sensory data captured by a phabrometer in testing samples with skin care products applied. In some embodiments, the cloud-network service supports a platform as a service (PaaS) architecture. In some embodiments, the cloud-network service includes a remote application operational environment that provides a plurality of remote skin care product evaluation applications. In some embodiments, the plurality of remote skin care product evaluation applications includes a hybrid remote skin care product evaluation application and a cloud remote skin care product evaluation application. The remote application operational environment provides the remote skin care product evaluation applications to enable one or more client computing devices to perform operations that create or read skin care product evaluation and efficacy information. In some embodiments, the hybrid remote skin care product evaluation application is associated with a corresponding hybrid program running on a processor of a cloud-network server. In some embodiments, the cloud remote skin care product evaluation application is associated with a corresponding cloud program running on the processor of the cloud-network server.

In some embodiments, the hybrid remote skin care product evaluation application enables a phabrometer client computing device to create skin care product test data that includes skin care product evaluation and efficacy information based on sensory data captured during a phabrometer test of a sample. In some embodiments, the corresponding hybrid program running on the processor of the cloud-network server receives the skin care product test data from the phabrometer client computing device, computes a set of skin care product evaluation results based on the received skin care product test data, and generates a set of skin care product comparison charts associated with the skin care product evaluation results.

In some embodiments, the hybrid remote skin care product evaluation application enables a non-phabrometer client computing device to direct a phabrometer to run a skin care product test in relation to a sample and provide skin care product test data in relation to the skin care product test to the non-phabrometer client computing device. In some embodiments, the corresponding hybrid program running on the processor of the cloud-network server receives the skin care product test data from the non-phabrometer client computing device, computes a set of skin care product evaluation results based on the received skin care product test data, and generates a set of skin care product comparison charts associated with the skin care product evaluation results.

In some embodiments, the cloud remote skin care product evaluation application enables client computing devices to read skin care product comparison charts associated with skin care product evaluation results captured by the phabrometer during a test of a sample. In some embodiments, a client computing device is associated with a display screen on which the product comparison charts are displayed.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein:

FIG. 4A conceptually illustrates a schematic view of a test sample holder apparatus in some embodiments of the phabrometer.

FIG. 4B conceptually illustrates a schematic view of the test sample holder apparatus during use in some embodiments of the phabrometer.

FIG. 5 conceptually illustrates a process in some embodiments for evaluating the efficacy of skin care products by way of an instrumental phabrometer approach to testing the skin care products.

DETAILED DESCRIPTION

Figure 1:
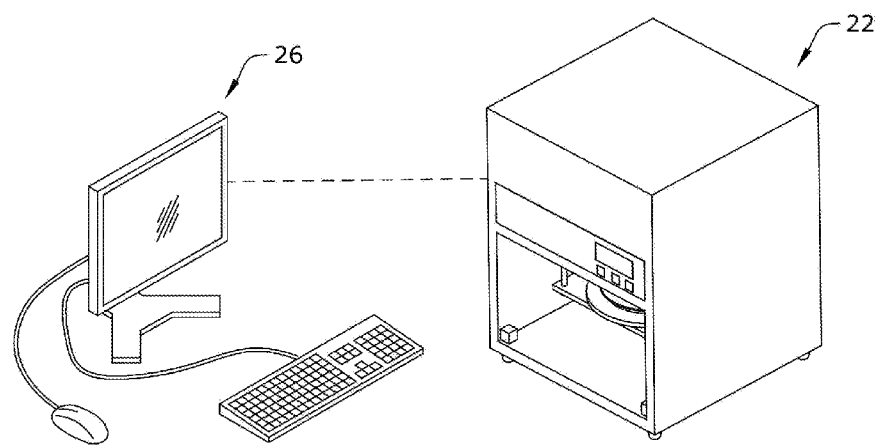
FIG. 1 conceptually illustrates a skin care product efficacy evaluation system in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications. Also, the description points to an instrument that is referred to as a phabrometer, phabrometer instrument, phabrometer device, phabrometer machine, phabrometer smart machine, phabrometer and (embedded) computing device, and/or phabrometer skin testing machine. The phabrometer instrument is a physical, tangible instrument. A related trademark exists, namely, PhabrOmeter®. The PhabrOmeter® trademark identifies the instrument that is a component of a skin care product efficacy evaluation system described in this disclosure and which is used in the process for evaluating skin care product efficacy, also described herein. Every effort has been made in this specification to clearly use conventional sentence-style case lettering for the term "phabrometer" when describing the instrument, and to conform to the case lettering style of the registered trademark PhabrOmeter® when noted in this description.

As stated above, manufacturers of skin care products typically make skin protection and improvement claims in support of the efficacy of their skin care products. However, existing methods of validating such claims lack objectivity or do not offer a consistent and stable testing platform. Of the several instruments that have been tried, none of them (to date) have successfully provided objective and consistent evidence of support for the efficacy of the claims being made. In other cases, the claims are simply dependent upon the subjective experiences of humans. Yet, human detection and discretion for changes in skin attributes are unreliable. These common problems shared by existing methods further include the question of whether to test the entire human face with a skin care product applied, or to just focus on certain key locations (not determined yet). Other problems follow, including the difficulty in conducting a repeatable test when every human face is unique, and therefore, hard to fix on, as seen in and among the various changes between different persons. This also suggests at least another problem, in that it is a challenge to know how many different skin attributes to test for making a reliable and complete judgment. Thus, people seeking objective evidence of the validity of skin care product claims are left in the dark.

Embodiments of the invention described in this specification solve such problems by a skin care product efficacy evaluation system and a process for evaluating efficacy of skin care products by way of an instrumental approach to testing skin care products. Several detailed examples of the skin care product efficacy evaluation system and process are described by reference to several figures included in this specification. The description of these examples and drawings provides a conceptual understanding of the instrumental approach employed in the inventive embodiments. In particular, reference is made to a phabrometer test instrument (or simply, a "phabrometer") that measures sensory properties and attributes of skin, synthetic skin, skin specimens, and/or other fibrous specimens. In some embodiments, the instrument-based method for evaluating efficacy of skin care products is performed in connection with the skin care product efficacy evaluation system. The skin care product efficacy evaluation system may include one or more phabrometer test machines which, along with other computing devices and/or networking devices, may be deployed in a non-networked environment, a closed-network environment, or a cloud-network environment.

In some embodiments, the process for evaluating efficacy of skin care products includes several steps to carry out operations of the instrumental approach to testing skin care products. In some embodiments, the process for evaluating efficacy of skin care products includes one or more steps for using the phabrometer to test samples with skin care products applied. In some embodiments, the process for evaluating efficacy of skin care products includes selecting a substrate treated with a skin care product. In some embodiments, the substrate includes a synthetic skin specimen. In some embodiments, after the selected substrate is treated with the skin care product, the process then tests the substrate by using the phabrometer to show skin performance numerically in terms of skin attributes, including skin softness, skin smoothness, skin resilience, and wrinkle resistance. In some embodiments, the phabrometer includes a computerized smart machine that tests a specimen quickly and analyzes the result based on an algorithm, and provides the outputs necessary and sufficient to completely characterize the skin performance.

In this specification, there are several descriptions of processes and methods that are performed by software running on computing device, such as a traditional computing device (e.g., computer, laptop, server, etc.) or a specialized computing device (e.g., a phabrometer smart machine with a test sample holder apparatus, sensors for capturing test data, a processing unit to perform run-time computation on captured test data and register addressing for data transmission and/or persistent storage, a memory unit (RAM), a permanent storage (on-board or externally connected), a network interface (wired and/or wireless), and peripheral device ports such as USB ports, audio input/output ports, video display ports, etc.). A graphical user interface may be implemented in a presentation layer of a software application that analyzes the captured test data, applies one or more test sample evaluation algorithms to the captured test data, and displays the results of the evaluation on a display screen for human review. Such a graphical user interface may be embedded as a module of the overall software application, or may run as a separate application that connects to the software application over a network. For instance, the graphical user interface may be designed as a desktop computer application or a mobile app (e.g., for a smartphone) for a user to connect to the phabrometer smart machine and perform one or more evaluations of prepared specimens. However, it should be noted that for the purposes of the embodiments described in this specification, the word "method" is used interchangeably with the word "process". Methods are described, therefore, by reference to example processes that conceptually illustrate process steps for evaluating the efficacy of skin care products by way of an instrumental approach to testing the skin care products.

In this specification, the disclosed process for evaluating efficacy of skin care products by way of an instrumental approach to testing skin care products (also referred to as the phabrometer-based skin care product evaluation process, the phabrometer-based skin care product testing process, or simply the phabrometer-based process) and the skin care product efficacy evaluation system are described at a level of detail that, in many instances, goes beyond the corresponding descriptions in the related provisional application, which this application claims benefit to, namely, U.S. Provisional Patent Application 62/157,739, entitled "An instrument enabling evaluation of efficacy of skin care products," filed May 6, 2015. However, a person skilled in the art relevant to the present invention would appreciate that the further details and descriptions provided in this specification are directly related to the descriptions in the specification for U.S. Provisional Patent Application 62/157,739, wherein a phabrometer test instrument (or simply, "phabrometer") and associated process for evaluating efficacy of skin care products were described in such a manner as to relate the fundamental steps and operations to the novel aspects of the present invention. In those descriptions, as in the descriptions of the novel aspects of the inventive embodiments for the present specification, the phabrometer-based skin care product evaluation process and the skin care product efficacy evaluation system are disclosed as using the phabrometer to carry out preliminary testing of substrate samples and specimens.

Several more detailed embodiments are described below. Section I describes instrumentation and hardware of phabrometer-based skin care product efficacy evaluations. Section II describes a process for evaluating the efficacy of skin care products by way of an instrumental approach to testing the skin care products. Next, Section III includes examples of graphical displays showing quantitative (numerical) results of testing several samples to evaluate the efficacy of a variety of skin care products applied to the samples. Next, Section IV describes two examples of cloud-based skin care product efficacy evaluation systems that host remote application cloud-compute environments for evaluating phabrometer-based skin care product data to determine efficacy of skin care products. Lastly, Section IV describes an electronic system that implements some embodiments of the invention.

I. Phabrometer-Based Skin Care Product Efficacy Evaluation

As noted above, the instrument-based method for evaluating efficacy of skin care products is performed in connection with a skin care product efficacy evaluation system that includes a specific testing instrument, namely, a phabrometer.

By way of example, FIG. 1 conceptually illustrates a skin care product efficacy evaluation system. As shown in this figure, the skin care product efficacy evaluation system includes a phabrometer 22 and a data computation and display system 26.

Figure 2:
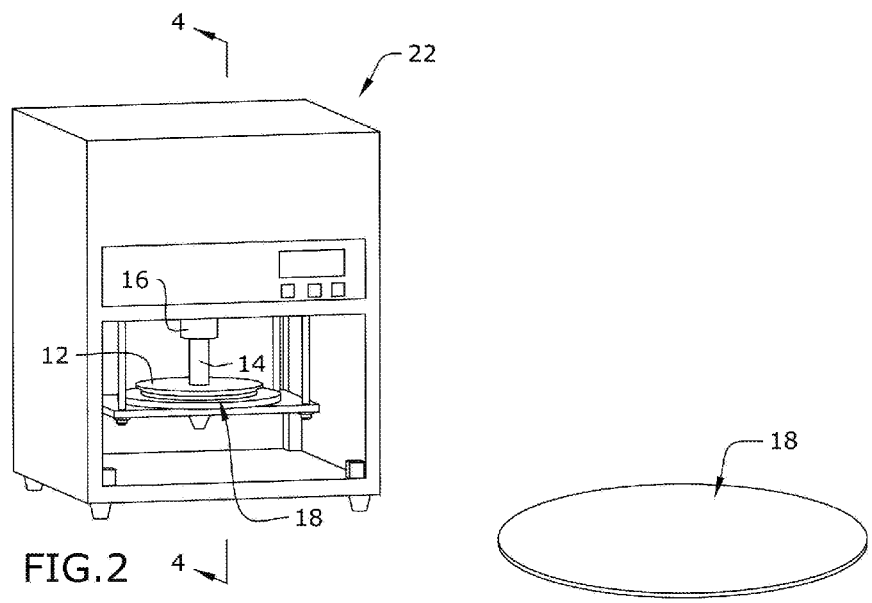
FIG. 2 conceptually illustrates a phabrometer during use in some embodiments.

Turning to FIG. 2, the phabrometer 22 is conceptually illustrated during use. As shown in this figure, the phabrometer 22 is used in connection with a test of a sample specimen 18. A transducer 16, a pushing rod 14, and a pressure plate 12 are also shown as testing components of the phabrometer 22.

The phabrometer is an instrument that is capable for testing attributes and qualities of textile products, fabrics, and other specimens. The phabrometer is described in China Patent number 2011 1 0260522.1, the entirety of which is incorporated herein by reference. In some embodiments, the process for evaluating efficacy of skin care products includes selecting a substrate treated with a skin care product. In some embodiments, the substrate includes one of a synthetic skin specimen and a fabric sample.

Figure 3:
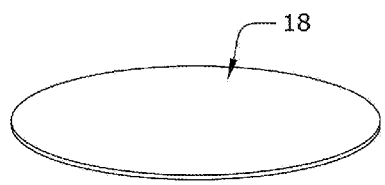
FIG. 3 conceptually illustrates a perspective view of an exemplary specimen in some embodiments.

By way of example, FIG. 3 conceptually illustrates a perspective view of an exemplary specimen 18 that may be used in connection with evaluating the efficacy of a skin care product applied to the specimen 18 and as tested by the phabrometer 22.

In some embodiments, the phabrometer that is used in testing skin care products is a revised and updated instrument that is optimized for use in testing attributes and qualities of skin (both natural skin and synthetic skin). The updated phabrometer therefore tests a specimen only once to obtain information related to a plurality of skin attributes and qualities. The phabrometer yields numerical results to describe the skin changes. The numerical results of the tests reflect the efficacy of the skin care product claims that may be made in any given type of skin care product. In addition to obtaining all the information needed in a single test, usage of the phabrometer shows good repeatability and sensitivity.

Since a human face is a difficult medium to use for testing, the phabrometer-based process can quickly test a specimen and analyze skin performance in a repeated fashion to demonstrate substantial conformity with test results. Data outliers, in some cases, may be excluded to obtain a more accurate reading of the tests, when performed repeatedly. Also, by using a synthetic skin specimen or fabric sample, there is no practical limit to the number of tests that can be performed. This is a huge advantage over tests that are performed on an actual human face because the human face is hard to repeatedly fix on. Countless differences exist between the skin of one human and another human, further increasing the challenges associated with obtaining accurate and objective test data on which to perform an evaluation of a skin care product.

By way of example, FIG. 4A conceptually illustrates a schematic view of a test sample holder apparatus of the phabrometer 22. The test sample holder apparatus shown in this figure includes a metal nozzle 10, a pressure plate 12, a pushing rod 14, and a transducer 16. In this illustration, a specimen 18 is shown between the metal nozzle 10 and the pressure plate 12, and configured to receive downward pressure from the pushing rod 14.

An example of such downward pressure being applied to the specimen 18 is conceptually illustrated in FIG. 4B. Specifically, the specimen 18 is positioned between the metal nozzle 10 and the pressure plate 12. The entire specimen 18 is tested when the pushing rod 14 applies downward pressure against a small, specific area of the specimen 18. However, the metal nozzle 10 and the pressure plate 12 are able to secure the remaining portion of the specimen 18 during the test. As can be seen in this figure, the specimen 18 is quickly tested with straightforward mechanical driver power forcing downward pressure on the specimen 18. This allows for the data to be quickly captured and analyzed by application of one or more specific algorithms. The results are then provided in a way that sufficiently and completely allows a human viewer or an automated process to understand the qualitative differences (and thereby deduce the actual efficacy of a given skin care product).

In some embodiments, after the selected substrate is treated with the skin care product, the process then tests the substrate by using the phabrometer to show skin performance numerically in terms of skin attributes, including skin softness, skin smoothness, skin resilience, and wrinkle resistance.

II. Process for Evaluating the Efficacy of Skin Care Products by Way of an Instrumental Approach to Testing the Skin Care Products By way of example, FIG. 5 conceptually illustrates a process 28 for evaluating the efficacy of skin care products by way of an instrumental phabrometer approach to testing the skin care products. As shown in this figure, the phabrometer-based process 28 for evaluating the efficacy of skin care products includes several steps during which operations are carried out in furtherance of testing a sample. The phabrometer-based process 28 starts with test preparation (at 30). During test preparation, the skin care product efficacy evaluation system warms up. This includes launching the software for interacting with the phabrometer-based process and testing samples. The software also allows for visual display of testing results. Additionally, the test preparation step includes sample preparation. As noted above, the sample may be a synthetic skin specimen (e.g., synthetic human skin) or a sample fabric (e.g., a synthetic leather-substitute fabric). A cream or another type of topical product may be applied (or skin care product).

Next, the phabrometer-based process 28 performs sample mounting (at 32). During sample mounting, the sample that was prepared during the first step (at 30) is placed in the test sample holder apparatus of the phabrometer. Examples of the test sample holder apparatus are described above by reference to FIGS. 4A and 4B. In addition to placing the sample in the test sample holder apparatus, the phabrometer-based process 28 includes record creation (for this particular sample, a new record created as each sample is tested) and test condition setting.

In some embodiments, the phabrometer-based process 28 then performs sample testing (at 34). During this stage, the test is started (e.g., the sample is already positioned in the phabrometer and the computation units and displays are warmed up and ready to be used). Thus, data processing occurs while the sample is tested. The types of testing that occur include several attributes of samples (skin or fabric), including smoothness, softness, resiliency, and wrinkle recovery percentage, among other such testable attributes of samples. When the data processing is complete, results are computed along each of the testing attributes/qualities, and output for display in a format that a human viewer can appreciate. For instance, a percentage improvement of the skin care product allows a human viewer to understand that application of a skin care product may result in a 10% greater skin softness quality as compared to no skin care product.

After the results of the testing are displayed, the phabrometer-based process 28 then determines (at 36) whether there are any more samples to test. When there are more samples to test, the phabrometer-based process 28 returns to the start to perform test preparation (at 30) with a new sample. Otherwise, when no more samples are to be tested, the phabrometer-based process 28 ends.

Embodiments of the phabrometer-based process for evaluating the efficacy of skin care products differ from and improve upon currently existing options. In particular, some embodiments of the phabrometer-based process differ by employing an instrumental approach which provides an objective, consistent, and measurable testing platform to evaluate the efficacy of skin care products. The phabrometer used in carrying out the steps of the process 28 is capable of testing a variety of sample types, including synthetic skin and any other suitable substrate. For example, a polymer membrane may be a suitable substrate. Additionally, the phabrometer provides reliable test data that is captured during testing of samples and then transmitted to a skin care product efficacy evaluation system to analyze the results based on one or more algorithms that quantify several sample attributes or qualities measured in the sample. An example of a skin care product efficacy evaluation system is described above, by reference to FIG. 1, which includes a phabrometer 22 and associated computation and display devices. The skin care product efficacy evaluation system then displays the results for a human viewer to review. In this way, the phabrometer-based process 28 and associated skin care product efficacy evaluation system provide all the outputs necessary and sufficient to completely characterize the performance and/or quality of a sample with a product applied to its surface, such as a skin care product applied to skin.

The phabrometer-based process for evaluating efficacy of skin care products of the present disclosure may be performed by an updated and revised phabrometer smart machine comprised of the following elements. This list of possible constituent elements is intended to be exemplary only and it is not intended that this list be used to limit the phabrometer of the present application to just these elements or the phabrometer-based process for evaluating efficacy of skin care products to just these steps. Persons having ordinary skill in the art relevant to the present disclosure may understand there to be equivalent elements or steps that may be substituted within the present disclosure without changing the essential function or operation of the phabrometer and/or the phabrometer-based process for evaluating efficacy of skin care products.

1. A properly selected substrate mimicking the actual skin and treated with a skin care product as the test sample (see e.g., the exemplary sample 24 illustrated in FIG. 3)

2. A specially designed test sample holder apparatus (see e.g., FIG. 4A), including at least the following: (a) a specially designed test nozzle (see e.g., the metal nozzle 10 described above by reference to FIG. 4A), (b) a pressure plate with selected weight based on sample type (see e.g., the pressure plate 12 described above by reference to FIG. 4A), (c) a pushing rod (see e.g., the pushing rod 14 described above by reference to FIG. 4A) connected to a transducer (described next), (d) a transducer (see e.g., the transducer 16 described above by reference to FIG. 4A) sending the force-time data to computer during testing, and, (e) the sample to be tested (see e.g., the sample 18 described above by reference to FIG. 4A or the exemplary specimen 24 described above by reference to FIG. 3).

3. A mechanical drive system that is electronically triggered to activate the pushing rod which pushes the sample through the test nozzle;

4. A pattern recognition algorithm in the computer to process and analyze the data;

5. A mechanism to output the results, such as a printer, a graphical display screen, a database to store the data and output the results to other output devices.

The phabrometer-based process for evaluating efficacy of skin care products of the present disclosure generally works by using the phabrometer to test samples treated with different skin care products, resulting in different sets of data that quantify qualitative differences in samples with and without skin care products applied. In this way, the efficacy of the skin care products can be established in an objective and consistent manner, specifically being quantified and compared in terms of one or more skin attributes. The logic operation/calculations are all embedded into the software algorithm for the proper operation of the system.

To make the phabrometer-based process work in practice, one may implement a software system with a hardware instrument-based testing platform. In this example, the instrument used to test samples is a phabrometer. A person skilled in the relevant art would appreciate that the type of smart machine used to test samples depends, at least in part, on the type of material of the sample being tested. Thus, according to the types of samples being tested, one would manufacture and develop the individual parts of the corresponding testing instrument, would program the computer software, and would implement hardware resources and design data communication architectures and networks, which would allow the testing instrument to capture the test data and provide the data for evaluation and comparison in light of one or more software applications that implement the algorithms described above. Also, the instrument would need to be assembled as described above and installed properly as a starting point. Then the instrument and associated hardware resources would need to be connected with the computer on which the software package is installed (assembled system and assembled phabrometer examples are described above by reference to FIGS. 1 and 2). In some embodiments, automation in sample preparation and sample feeding into the sample holder would accelerate the test speed. Furthermore, in some embodiments, the identical function can be performed if turning the sample holder upside down and pushing the sample from the bottom upward.

To use the phabrometer-based process of the present disclosure, one may simply turn on the phabrometer instrument and the computer, prepare the sample, and then mount the sample into the holder apparatus. When the software is started, a sample test can begin. It is possible to evaluate efficacy of a skin care product against no skin care product by running a test on a sample with the skin care product applied and then to run the same test against another sample without the skin care product applied. It is also possible to evaluate efficacy of several different skin care products in comparison with each other—that is, by running a test on each sample with a particular skin care product applied (each sample having a different skin care product applied).

Figure 6:
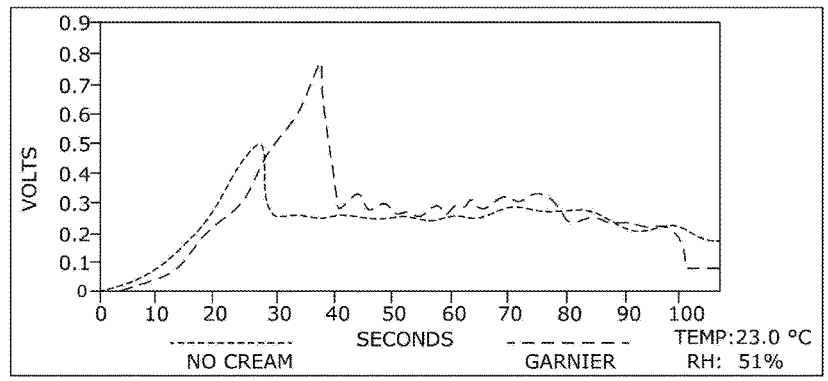
FIG. 6 conceptually illustrates an example graphical display in some embodiments showing results from a phabrometer-based test of a skin care product.
Figure 7:
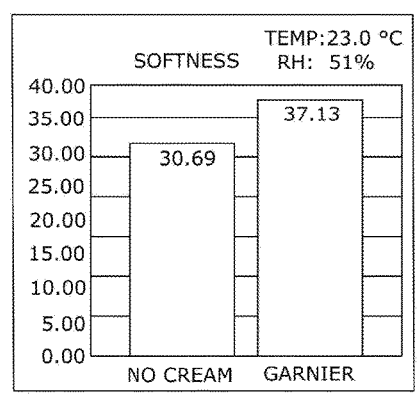
FIG. 7 conceptually illustrates an example graphical display in some embodiments showing a comparison of skin softness as tested by the phabrometer with and without a skin care product applied.
Figure 8:
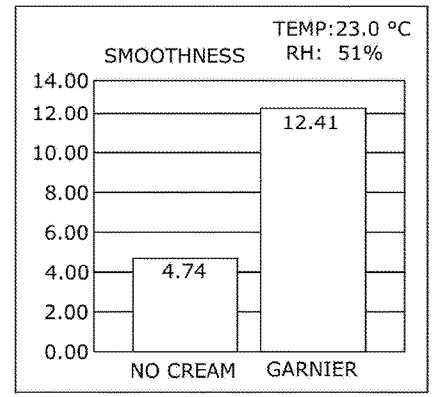
FIG. 8 conceptually illustrates an example graphical display in some embodiments showing a comparison of skin smoothness as tested by the phabrometer with and without a skin care product applied.
Figure 9:
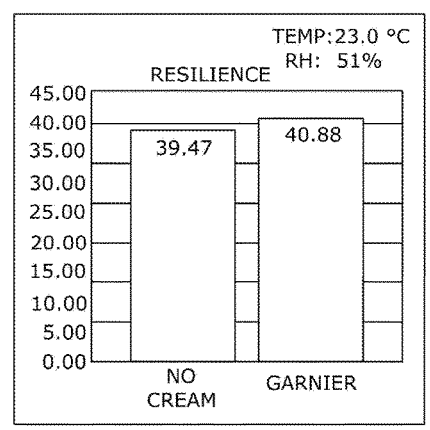
FIG. 9 conceptually illustrates an example graphical display in some embodiments showing a comparison of skin resilience as tested by the phabrometer with and without a skin care product applied.
Figure 10:
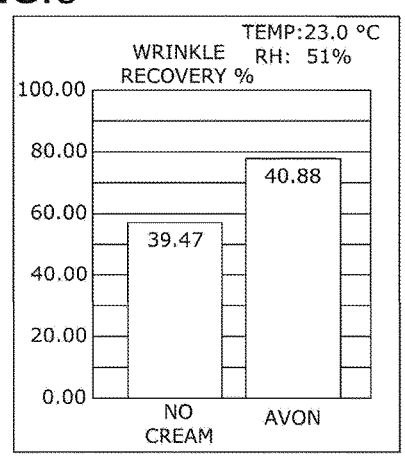
FIG. 10 conceptually illustrates an example graphical display in some embodiments showing a comparison of wrinkle recovery percentage as tested by the phabrometer with and without a skin care product applied.
Figure 11:
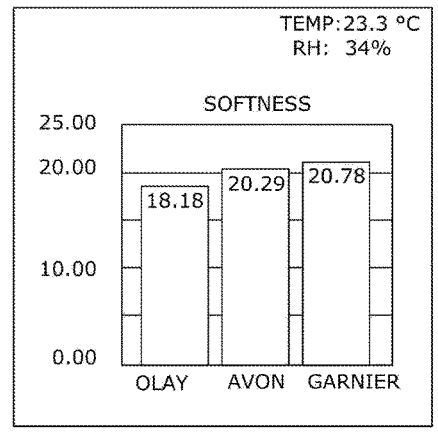
FIG. 11 conceptually illustrates an example graphical display in some embodiments showing a three-way comparison of skin softness as tested by the phabrometer in relation to three specimens that have different skin care products applied.
Figure 12:
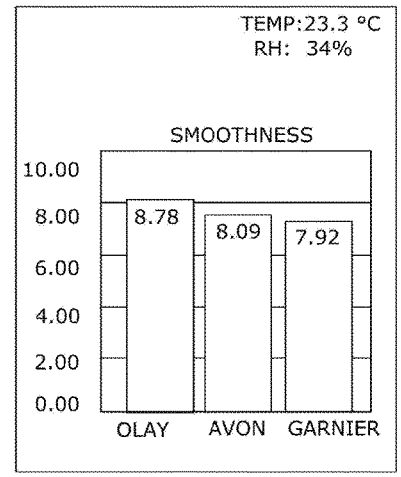
FIG. 12 conceptually illustrates an example graphical display in some embodiments showing a three-way comparison of skin smoothness as tested by the phabrometer in relation to three specimens that have different skin care products applied.
Figure 13:
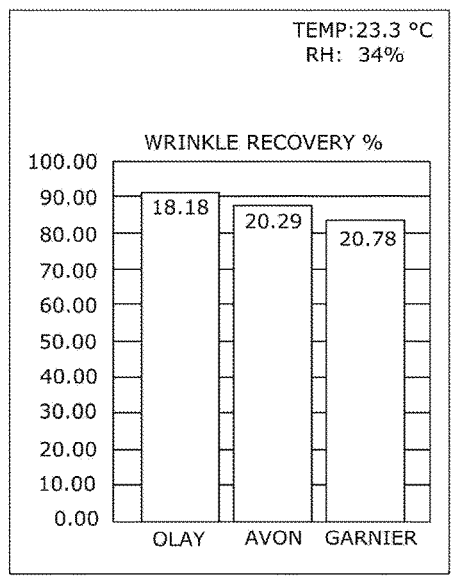
FIG. 13 conceptually illustrates an example graphical display in some embodiments showing a three-way comparison of skin wrinkle recovery percentage as tested by the phabrometer in relation to three specimens that have different skin care products applied.
Figure 14:
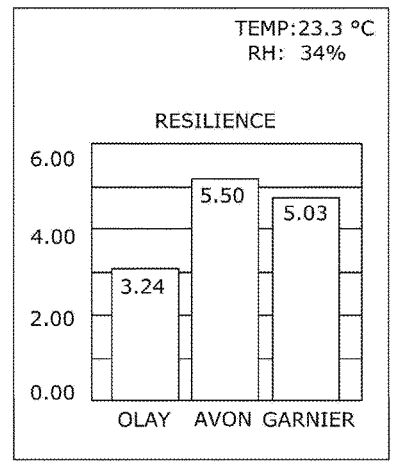
FIG. 14 conceptually illustrates an example graphical display in some embodiments showing a three-way comparison of skin resilience as tested by the phabrometer in relation to three specimens that have different skin care products applied.

III. Examples of Graphical Displays Showing Quantitative (Numerical) Results of Testing Samples with a Phabrometer to Evaluate the Efficacy of Skin Care Products Applied to the Samples Turning to FIGS. 6-14, several graphical displays are shown with example results of phabrometer-based sample tests. Specifically, FIG. 6 conceptually illustrates an example graphical display showing results from a phabrometer-based test of a skin care product, FIG. 7 conceptually illustrates an example graphical display showing a comparison of skin softness as tested by the phabrometer with and without a skin care product applied, FIG. 8 conceptually illustrates an example graphical display showing a comparison of skin smoothness as tested by the phabrometer with and without a skin care product applied, FIG. 9 conceptually illustrates an example graphical display showing a comparison of skin resilience as tested by the phabrometer with and without a skin care product applied, FIG. 10 conceptually illustrates an example graphical display showing a comparison of wrinkle recovery percentage as tested by the phabrometer with and without a skin care product applied, FIG. 11 conceptually illustrates an example graphical display showing a three-way comparison of skin softness as tested by the phabrometer in relation to three specimens that have different skin care products applied, FIG. 12 conceptually illustrates an example graphical display showing a three-way comparison of skin smoothness as tested by the phabrometer in relation to three specimens that have different skin care products applied, FIG. 13 conceptually illustrates an example graphical display showing a three-way comparison of skin wrinkle recovery percentage as tested by the phabrometer in relation to three specimens that have different skin care products applied, and FIG. 14 conceptually illustrates an example graphical display showing a three-way comparison of skin resilience as tested by the phabrometer in relation to three specimens that have different skin care products applied. As these drawings demonstrate, a person viewing the results of the phabrometer-based process can readily understand the attribute differences between tested samples.

IV. Cloud-Based Skin Care Product Efficacy Evaluation System

In some embodiments, the skin care product efficacy evaluation system provides an online platform that hosts an application service for evaluating skin care product efficacy based on skin care product testing performed by a phabrometer. In some embodiments, the online platform is based on a platform as a service (PaaS) cloud-network architecture. In some embodiments, the skin care product efficacy evaluation system includes a set of client computing devices comprising at least one phabrometer, a set of cloud server computing devices, and one or more host application databases, a set of skin care product evaluation servers, a cloud remote application database, and a hybrid remote application database.

The need for an online platform depends on a variety of factors, including expected usage, privacy concerns, industrial and business needs, etc. For instance, one client is a phabrometer testing machine that performs operations on synthetic skin. There are several sensors and a computer included in the overall phabrometer for gathering raw data during the synthetic skin tests and tabulating/computing numerical data results. When there is no cloud-based service, the phabrometer performs all computations and generates are charts and reports about the skin tests. However, when the skin care product efficacy evaluation system is deployed as a cloud-based service, all of the data transmission and storage requirements of phabrometer-based skin care product evaluations becomes an issue of concern (privacy, scalability, persistence, etc.). Thus, one or more operational requirements may be present for deployment of the system.

In some embodiments, a plurality of operational environments are supported by the PaaS cloud-network architecture of the skin care product efficacy evaluation system. In some embodiments, the plurality of operational environments include a cloud-compute operational environment and a remote application operational environment. The cloud-compute operational environment provides cloud server-based computation and processing of client requests.

The remote application operational environment provides a plurality of remote skin care product evaluation applications. In some embodiments, the plurality of remote skin care product evaluation applications includes a hybrid remote skin care product evaluation application and a cloud remote skin care product evaluation application. The remote application operational environment provides the remote skin care product evaluation applications to enable one or more client computing devices to perform operations that create or read skin care product evaluation and efficacy information. In some embodiments, the hybrid remote skin care product evaluation application is associated with a corresponding hybrid program running on a processor of a cloud-network server. In some embodiments, the cloud remote skin care product evaluation application is associated with a corresponding cloud program running on the processor of the cloud-network server.

In some embodiments, the hybrid remote skin care product evaluation application enables a phabrometer client computing device to create skin care product test data that includes skin care product evaluation and efficacy information based on sensory data captured during a phabrometer test of a sample. In some embodiments, the corresponding hybrid program running on the processor of the cloud-network server receives the skin care product test data from the phabrometer client computing device, computes a set of skin care product evaluation results based on the received skin care product test data, and generates a set of skin care product comparison charts associated with the skin care product evaluation results.

In some embodiments, the hybrid remote skin care product evaluation application enables a non-phabrometer client computing device to direct a phabrometer to run a skin care product test in relation to a sample and provide skin care product test data in relation to the skin care product test to the non-phabrometer client computing device. In some embodiments, the corresponding hybrid program running on the processor of the cloud-network server receives the skin care product test data from the non-phabrometer client computing device, computes a set of skin care product evaluation results based on the received skin care product test data, and generates a set of skin care product comparison charts associated with the skin care product evaluation results.

In some embodiments, the cloud remote skin care product evaluation application enables client computing devices to read skin care product comparison charts associated with skin care product evaluation results captured by the phabrometer during a test of a sample. In some embodiments, a client computing device is associated with a display screen on which the product comparison charts are displayed.

Figure 15:
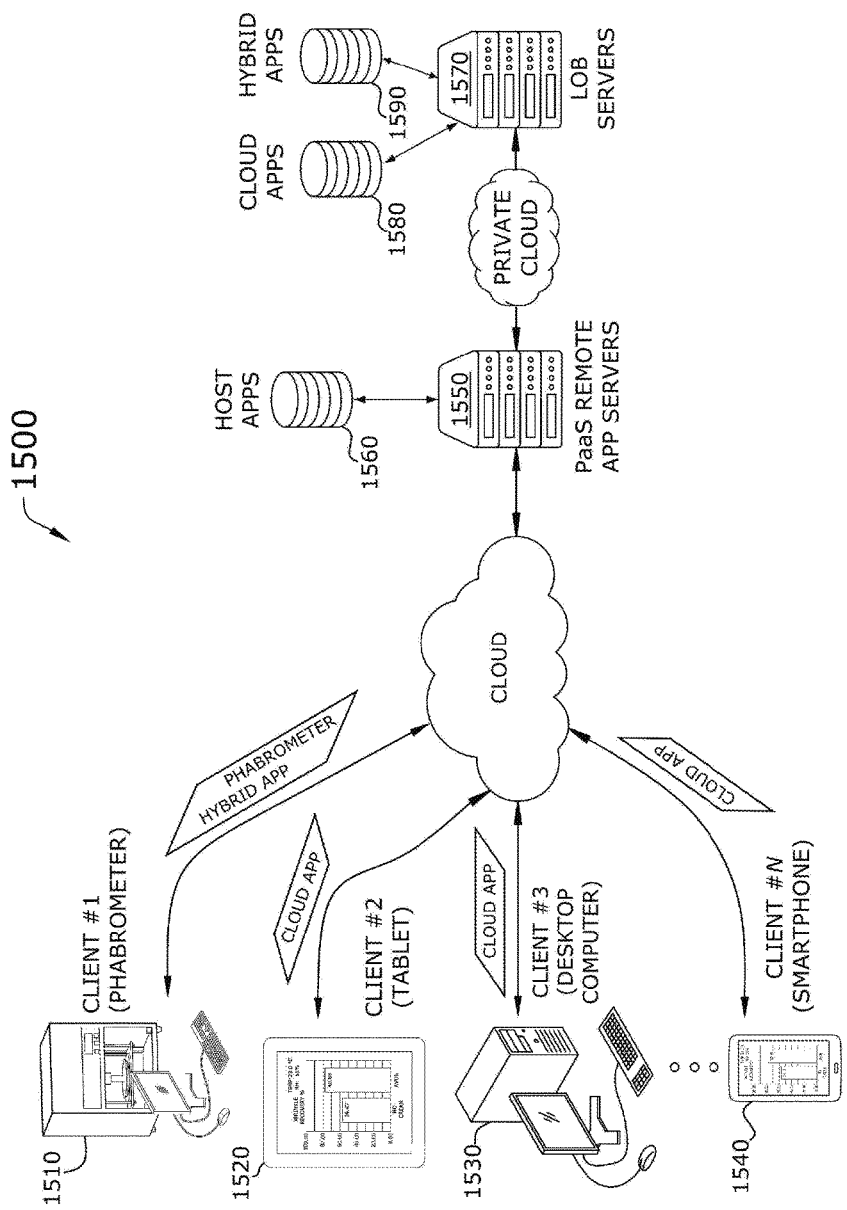
FIG. 15 conceptually illustrates an architecture of a cloud-based skin care product efficacy evaluation system that hosts a remote application cloud-compute environment for evaluating phabrometer-based skin care product data and determining efficacy of skin care products in some embodiments.

By way of example, FIG. 15 conceptually illustrates an architecture of a cloud-based skin care product efficacy evaluation system 1500 that hosts a remote application cloud-compute environment for evaluating phabrometer-based skin care product data and determining efficacy of skin care products. As shown in this figure, the cloud-based skin care product efficacy evaluation system 1500 includes a set of client computing devices 1510-1540, a set of cloud server computing devices 1550, a host application database 1560, a set of skin care product evaluation servers 1570 (LOB servers, or line-of-business servers), a cloud remote application database 1580, and a hybrid remote application database 1590. The set of client computing devices 1510-1540 connect over the Internet to the set of cloud server computing devices 1550 in relation to skin care product evaluation requests that involve at least one of hybrid remote application processing and cloud remote application processing.

The set of cloud server computing devices 1550 connects over a private cloud-network to at least one skin care product evaluation server computing device 1570 associated with a specific phabrometer that carries out the skin care product test. In this example, the specific phabrometer is client computing device 1510.

Then skin care product evaluation server computing device 1570 retrieves remote applications that correspond to the remote application processing needs of the set of cloud server computing devices 1550. This relates back to the original request from each client computing device. That is, a specific type of remote application is transmitted back to the requesting client computing device based on the request made by the client computing device.

For instance, in this example, CLIENT #1 is the phabrometer client computing device 1510 and may have made a request for a remote application that allows for operations outside of the cloud-server environment, specifically in furtherance of capturing sensory data obtained during skin care product evaluation tests of skin samples.

Accordingly, when the remote application processing needs of the set of cloud server computing devices 1550 include hybrid remote application processing, the skin care product evaluation server computing device 1570 retrieves the hybrid remote application from the hybrid remote application database 1590 and provides the hybrid remote application to the set of cloud server computing devices 1550. The set of cloud server computing devices 1550 thereafter sends the hybrid remote application to the requesting client computing device, which in this figure is only the phabrometer client computing device 1510.

In contrast, some client requests are only of the "read-only" sort, where operations on the data outside of the cloud are not requested. For example, CLIENT #2 (the tablet client computing device 1520), CLIENT #3 (the desktop client computing device 1530), and CLIENT #N (the smartphone client computing device 1540) may have made requests for remote applications that just display the results of data processing in the cloud. For instance, the client computing devices 1520-1540 (CLIENT#2, CLIENT #3, and CLIENT #N) may have requested to see the results of a skin care product evaluation and efficacy test run and compare to other such test runs. Note that in this figure, the remote application corresponding to the client computing device request or need is shown in a parallelogram shape.

Therefore, when the remote application processing needs of the set of cloud server computing devices 1550 include cloud remote application processing, the skin care product evaluation server computing device 1570 retrieves the cloud remote application from the cloud remote application database 1580 and provides the cloud remote application to the set of cloud server computing devices 1550. The set of cloud server computing devices 1550 thereafter sends the cloud remote application to the requesting client computing device. In this figure, each of other client computing devices 1520-1540 receive the cloud remote application.

In some embodiments, the cloud-network deployment includes a private cloud network that is associated with a specific phabrometer and which includes limitations on user and device access. When multiple phabrometers are connected to the cloud server, the cloud-network deployment includes a private cloud network for each phabrometer, with no sharing of data or intermingling of users/devices, unless specifically permitted by access rules for each private cloud network. By offering a variety of remote applications to process cloud computing requests from clients, the skin care product efficacy evaluation system 1500 is able to satisfy computing hardware and software needs for highly scalable processing and high volume data persistence.

Any network framework that could be deployed by the skin care product efficacy evaluation system 1500 would need to at least provide support for remote application accessibility and cloud computing functionality. For example, Microsoft Azure® provides a web service model (Microsoft Azure® RemoteApp®) that can be configured for public cloud application service, private cloud application service, or hybrid (mixed) cloud application service. Microsoft Azure® and Microsoft Azure RemoteApp® are Microsoft® product offerings.

Microsoft Azure® itself supports at least three general architectures for its more specific cloud service. There are databases and hosted virtual machines in the backend, but in theory, they can limit operations from different types of client computing devices. For example, the phabrometer with embedded computer needs to provide the raw sensor data to the cloud server, but other client computing devices (e.g., tablets, mobile devices, etc.) may have implementations that are supported for data access and reading, but not necessarily for data computation outside the cloud.

Figure 16:
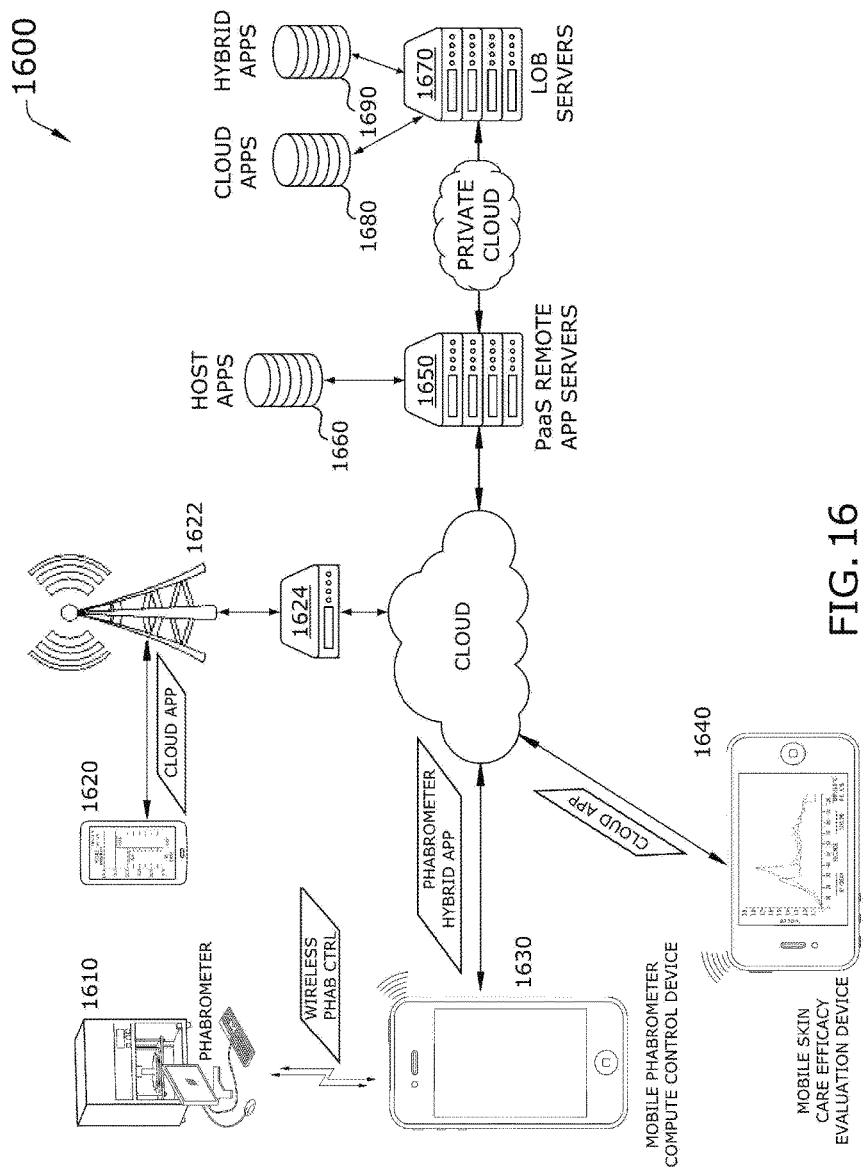
FIG. 16 conceptually illustrates an architecture of another cloud-based skin care product efficacy evaluation system that hosts a remote application cloud-compute environment for evaluating phabrometer-based skin care product data and determining efficacy of skin care products in some embodiments.

Turning to another example of a cloud-based skin care product efficacy evaluation system, FIG. 16 conceptually illustrates an architecture of another cloud-based skin care product efficacy evaluation system 1600 that hosts a remote application cloud-compute environment for evaluating phabrometer-based skin care product data and determining efficacy of skin care products.

As shown in this figure, the cloud-based skin care product efficacy evaluation system 1600 includes a phabrometer instrument 1610, a set of client computing devices 1620-1640, a wireless communication point 1622 (e.g., a cell tower for cellular data communication), a gateway 1624, a set of cloud server computing devices 1650, a host application database 1660, a set of skin care product evaluation servers 1670 (LOB servers, or line-of-business servers), a cloud remote application database 1680, and a hybrid remote application database 1690.

The example shown in this figure includes a phabrometer instrument 1610 for performing skin care product evaluations but which is not connected to the cloud directly. Also, client computing device 1620 connects to the wireless communication point 1622 to connect to the cloud server computing devices 1650. The connection request from the client computing device 1620 is transmitted to the gateway 1624, which secures the connection for the client computing device 1620 to the cloud server computing devices 1650.

Two of the client computing devices, namely client computing device 1630 (the MOBILE PHABROMETER COMPUTE CONTROL DEVICE) and client computing device 1640 (the MOBILE SKIN CARE EFFICACY EVALUATION DEVICE), connect over the Internet to the set of cloud server computing devices 1650 in relation to skin care product evaluation requests that involve at least one of hybrid remote application processing and cloud remote application processing. In this case, the client computing device 1640 (the MOBILE SKIN CARE EFFICACY EVALUATION DEVICE) may have requested results from a specific skin care product evaluation. Therefore, the cloud remote application was provided to the client computing device 1640.

On the other hand, the client computing device 1630 (the MOBILE PHABROMETER COMPUTE CONTROL DEVICE) may be requested operational control of the phabrometer 1610 in connection with backend cloud processing of the data retrieved during the skin care product evaluation. Therefore, the hybrid remote application was provided to the client computing device 1630, which enables the client computing device 1630 to use resources outside of the specific cloud network environment, instead of merely consuming data from the cloud.

While the cloud-network architectures of the skin care product efficacy evaluation systems shown in FIG. 15 and FIG. 16 are only two examples of several possible deployments, a person skilled in the art would appreciate that these examples are only meant to describe inventive embodiments where a system is deployed over a network and that any number of other deployments may be conceived and understood as being related to the inventive embodiments described above. Therefore, the above-described embodiments of the invention (beyond those described by reference to FIGS. 15 and 16) are presented for purposes of illustration and not of limitation. While these embodiments of the invention have been described with reference to numerous specific details, one of ordinary skill in the art will recognize that the invention can be embodied in other specific forms without departing from the spirit of the invention. For instance, several examples described in this specification relate to evaluating the efficacy of skin care product claims in view of an instrumental approach to testing such skin care products on skin specimens, it is noted that embodiments of the skin care product evaluation system, the phabrometer-based process, and the phabrometer instrument itself are able to work with any type of prepared sample in order to test the sample and thereby determine the efficacy of performance claims of the skin care products. This would therefore include, for example, any membrane product with similar sensory performance requirements. Examples of membrane products that can be evaluated by performing the steps of the phabrometer-based process and using a phabrometer include, without limitation, textiles, leather, facial and other tissues, hygiene products, etc.

V. Electronic System

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "application", "app", and "mobile app" (referred to below as "software") are meant to include firmware residing in read-only memory or applications stored in magnetic storage, which can be read into memory for processing by a processor, such as the processor of a mobile computing device or a mobile communication device, such as a smartphone, a hand-held computing device, or a tablet computing device (referred to simply as a "mobile device"), or the processor of a traditional computing device, such as a server computer, a desktop computer, or a laptop computer (referred to simply as a "computer"). Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 17:
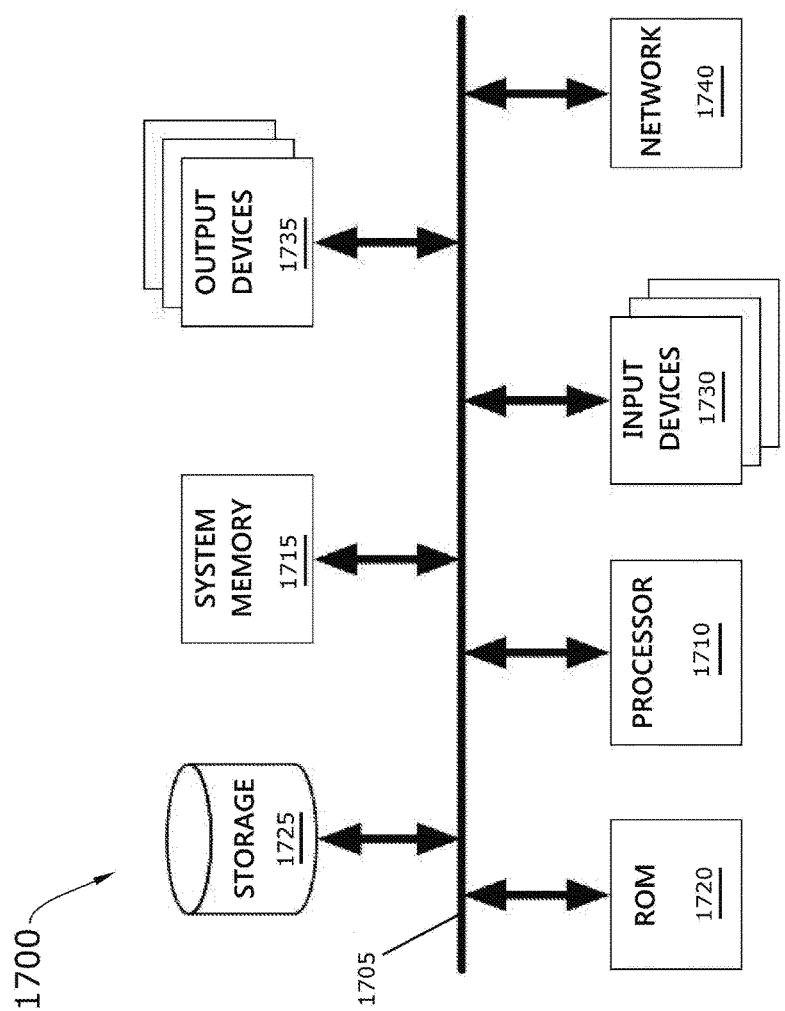
FIG. 17 conceptually illustrates an electronic system with which some embodiments of the invention are implemented.

FIG. 17 conceptually illustrates an electronic system 1700 with which some embodiments of the invention are implemented. The electronic system 1700 may be a computer, mobile device, tablet, phone, PDA, or any other sort of electronic device. Such an electronic system includes various types of computer readable media and interfaces for various other types of computer readable media. Electronic system 1700 includes a bus 1705, processing unit(s) 1710, a system memory 1715, a read-only 1720, a permanent storage device 1725, input devices 1730, output devices 1735, and a network 1740.

The bus 1705 collectively represents all system, peripheral, and chipset buses that communicatively connect the numerous internal devices of the electronic system 1700. For instance, the bus 1705 communicatively connects the processing unit(s) 1710 with the read-only 1720, the system memory 1715, and the permanent storage device 1725.

From these various memory units, the processing unit(s) 1710 retrieves instructions to execute and data to process in order to execute the processes of the invention. The processing unit(s) may be a single processor or a multi-core processor in different embodiments.

The read-only-memory (ROM) 1720 stores static data and instructions that are needed by the processing unit(s) 1710 and other modules of the electronic system. The permanent storage device 1725, on the other hand, is a read-and-write memory device. This device is a non-volatile memory unit that stores instructions and data even when the electronic system 1700 is off. Some embodiments of the invention use a mass-storage device (such as a magnetic or optical disk and its corresponding disk drive) as the permanent storage device 1725.

Other embodiments use a removable storage device (such as a floppy disk or a flash drive) as the permanent storage device 1725. Like the permanent storage device 1725, the system memory 1715 is a read-and-write memory device. However, unlike storage device 1725, the system memory 1715 is a volatile read-and-write memory, such as a random access memory. The system memory 1715 stores some of the instructions and data that the processor needs at runtime. In some embodiments, the invention's processes are stored in the system memory 1715, the permanent storage device 1725, and/or the read-only 1720. For example, the various memory units include instructions for processing appearance alterations of displayable characters in accordance with some embodiments. From these various memory units, the processing unit(s) 1710 retrieves instructions to execute and data to process in order to execute the processes of some embodiments.

The bus 1705 also connects to the input and output devices 1730 and 1735. The input devices enable the user to communicate information and select commands to the electronic system. The input devices 1730 include alphanumeric keyboards and pointing devices (also called "cursor control devices"). The output devices 1735 display images generated by the electronic system 1700. The output devices 1735 include printers and display devices, such as cathode ray tubes (CRT) or liquid crystal displays (LCD). Some embodiments include devices such as a touchscreen that functions as both input and output devices.

Finally, as shown in FIG. 17, bus 1705 also couples electronic system 1700 to a network 1740 through a network adapter (not shown). In this manner, the computer can be a part of a network of computers (such as a local area network ("LAN"), a wide area network ("WAN"), or an intranet), or a network of networks (such as the Internet). Any or all components of electronic system 1700 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, many of the drawings conceptually illustrate computer-based instruments and testing machines which facilitate the steps of one or more processes. In each case, the machine specific needs and testing requirements may necessitate that the specific operations of a process not be performed in the exact order shown and described. Specific operations may not be performed in one continuous series of operations, and different specific operations may be performed in different embodiments. Furthermore, the process could be implemented using several sub-processes, or as part of a larger macro process. Thus, one of ordinary skill in the art would understand that the invention is not to be limited by the foregoing illustrative details, but rather is to be defined by the appended claims.

We claim:

1. A system to objectively evaluate the efficacy of a skin care product, said system comprising:
   a first sample membrane treated with a skin care product;
   a second sample membrane with no skin care product applied;
   a phabrometer comprising a transducer, a pushing rod, and a pressure plate; and
   a data computation and display system comprising a computer screen and a computerized smart machine that includes a processor, a memory storage, and a program that is stored in the memory storage and which, when running on the processor of the computerized smart machine, evaluates the efficacy of the skin care product, said program comprising sets of instructions for (i) creating a skin care product efficacy test project to record sets of membrane attribute data resulting from a first phabrometer-based test of the first sample membrane with the skin care product applied and a second phabrometer-based test of the second sample membrane with no skin care product applied, (ii) configuring a set of test condition settings that defines a scope of testing by the phabrometer for each of the first phabrometer-based test of the first sample membrane and the second phabrometer-based test of the second sample membrane, (iii) capturing a first set of membrane attribute data while the phabrometer performs the first phabrometer-based test of the first sample membrane with the skin care product applied, (iv) calculating an efficacy value for each membrane attribute in the first set of membrane attribute data, (v) capturing a second set of membrane attribute data while the phabrometer performs the second phabrometer-based test of the second sample membrane without the skin care product applied, (vi) calculating baseline value for each membrane attribute in the second set of membrane attribute data, and (vii) displaying a set of skin care product efficacy charts on the computer screen that demonstrate the efficacy of the skin care product in comparison with no skin care product.

2. The system of claim 1, wherein each set of membrane attribute data corresponds to a set of skin attributes.

3. The system of claim 2, wherein the set of skin attributes comprise skin softness, skin smoothness, skin resilience, and wrinkle recovery.

4. The system of claim 3, wherein the set of instructions for displaying a set of skin care product efficacy charts on the computer screen comprises a set of instructions for displaying a skin softness efficacy chart comprising a first graphical element with a size that corresponds to the calculated efficacy value for the skin softness membrane attribute and a second graphical element with a size that corresponds to the calculated baseline value for the skin softness membrane attribute.

5. The system of claim 3, wherein the set of instructions for displaying a set of skin care product efficacy charts on the computer screen comprises a set of instructions for displaying a skin smoothness efficacy chart comprising a first graphical element with a size that is weighted according to the calculated efficacy value for the skin smoothness membrane attribute and a second graphical element with a size that is weighted according to the calculated baseline value for the skin smoothness membrane attribute.

6. The system of claim 3, wherein the set of instructions for displaying a set of skin care product efficacy charts on the computer screen comprises a set of instructions for displaying a skin resilience efficacy chart comprising a first graphical element with a size that is weighted according to the calculated efficacy value for the skin resilience membrane attribute and a second graphical element with a size that is weighted according to the calculated baseline value for the skin resilience membrane attribute.

7. The system of claim 3, wherein the set of instructions for displaying a set of skin care product efficacy charts on the computer screen comprises a set of instructions for displaying a wrinkle recovery efficacy chart comprising a first graphical element with a size that is weighted according to the calculated efficacy value for the wrinkle recovery membrane attribute and a second graphical element with a size that is weighted according to the calculated baseline value for the wrinkle recovery membrane attribute.

8. A non-transitory computer readable medium storing a program which, when executed by a processor of a computing device embedded in a phabrometer smart machine, evaluates the efficacy of a plurality of skin care products by way of a phabrometer that tests a sample membrane for each of the plurality of skin care products, said program comprising sets of instructions for:

creating a skin care product efficacy test project to record sets of membrane attribute data resulting from phabrometer-based tests of a plurality of sample membranes with the plurality of skin care products applied, wherein each skin care product in the plurality of skin care products is applied to only one sample membrane in the plurality of sample membranes;

configuring a set of test condition settings that defines a scope of testing by the phabrometer for the phabrometer-based tests of the plurality of sample membranes;

providing the set of test condition settings to the processor of the computing device embedded in the phabrometer smart machine to set runtime configuration for testing the plurality of sample membranes;

directing the phabrometer smart machine, by the computing device, to sequentially test the plurality of sample membranes, wherein each successive sample membrane is tested, by the phabrometer smart machine, by capturing a set of membrane attribute data for the sample membrane and calculating, by the computing device, an efficacy value for each membrane attribute of the sample membrane; and displaying, on a computer screen communicably connected to the computing device, a set of skin care product efficacy charts that compare the efficacy of the plurality of skin care products for each set of membrane attribute data.

9. The non-transitory computer readable medium of claim 8, wherein each set of membrane attribute data corresponds to a set of skin attributes comprising skin softness, skin smoothness, wrinkle recovery, and skin resilience.

10. The non-transitory computer readable medium of claim 9, wherein the set of instructions for displaying, on the computer screen communicably connected to the computing device, a set of skin care product efficacy charts comprises sets of instructions for:

displaying, on the computer screen communicably connected to the computing device, a skin softness efficacy chart comprising a plurality of skin softness graphical elements corresponding to the plurality of skin care products, each skin softness graphical element having a size that is weighted according to the calculated efficacy value of a skin softness membrane attribute for the captured set of membrane attribute data of the sample membrane with the corresponding skin care product applied;

displaying, on the computer screen communicably connected to the computing device, a skin smoothness efficacy chart comprising a plurality of skin smoothness graphical elements corresponding to the plurality of skin care products, each skin smoothness graphical element having a size that is weighted according to the calculated efficacy value of a skin smoothness membrane attribute for the captured set of membrane attribute data of the sample membrane with the corresponding skin care product applied;

displaying, on the computer screen communicably connected to the computing device, a wrinkle recovery efficacy chart comprising a plurality of wrinkle recovery graphical elements corresponding to the plurality of skin care products, each wrinkle recovery graphical element having a size that is weighted according to the calculated efficacy value of a wrinkle recovery membrane attribute for the captured set of membrane attribute data of the sample membrane with the corresponding skin care product applied; and displaying, on the computer screen communicably connected to the computing device, a skin resilience efficacy chart comprising a plurality of skin resilience graphical elements corresponding to the plurality of skin care products, each skin resilience graphical element having a size that is weighted according to the calculated efficacy value of a skin resilience membrane attribute for the captured set of membrane attribute data of the sample membrane with the corresponding skin care product applied.

* * * * *